(12) United States Patent
Nimitz

(10) Patent No.: US 8,287,579 B2
(45) Date of Patent: Oct. 16, 2012

(54) METHOD OF USING CRYOGENIC COMPOSITIONS FOR COOLING HEATED SKIN

(75) Inventor: Jonathan Shelley Nimitz, Albuquerque, NM (US)

(73) Assignee: Thermage, Inc., Hayward, CA (US)

( * ) Notice: Subject to any disclaimer, the term of this patent is extended or adjusted under 35 U.S.C. 154(b) by 1034 days.

(21) Appl. No.: 12/211,537

(22) Filed: Sep. 16, 2008

(65) Prior Publication Data

US 2009/0076572 A1   Mar. 19, 2009

Related U.S. Application Data

(60) Provisional application No. 60/972,873, filed on Sep. 17, 2007.

(51) Int. Cl.
*A61F 7/00* (2006.01)

(52) U.S. Cl. .................................................. 607/104

(58) Field of Classification Search ............. 606/41–42, 606/45–50; 607/97, 101–105
See application file for complete search history.

(56) References Cited

U.S. PATENT DOCUMENTS

| | | | |
|---|---|---|---|
| 5,605,647 A | 2/1997 | Nimitz et al. | |
| 5,611,210 A | 3/1997 | Nimitz et al. | |
| 5,705,771 A * | 1/1998 | Flynn et al. | 149/1 |
| 5,714,654 A * | 2/1998 | Yamamoto et al. | 570/170 |
| 5,716,549 A | 2/1998 | Nimitz et al. | |
| 5,755,753 A | 5/1998 | Knowlton | |
| 5,871,524 A | 2/1999 | Knowlton | |
| 5,919,219 A | 7/1999 | Knowlton | |
| 5,948,011 A | 9/1999 | Knowlton | |
| 6,241,753 B1 | 6/2001 | Knowlton | |
| 6,270,689 B1 | 8/2001 | Nimitz | |
| 6,311,090 B1 | 10/2001 | Knowlton | |
| 6,350,276 B1 | 2/2002 | Knowlton | |
| 6,377,854 B1 | 4/2002 | Knowlton | |
| 6,377,855 B1 | 4/2002 | Knowlton | |
| 6,381,497 B1 | 4/2002 | Knowlton | |
| 6,381,498 B1 | 4/2002 | Knowlton | |
| 6,387,380 B1 | 5/2002 | Knowlton | |
| 6,405,090 B1 | 6/2002 | Knowlton | |
| 6,413,255 B1 | 7/2002 | Stern | |
| 6,425,912 B1 | 7/2002 | Knowlton | |
| 6,430,446 B1 | 8/2002 | Knowlton | |
| 6,438,424 B1 | 8/2002 | Knowlton | |
| 6,453,202 B1 | 9/2002 | Knowlton | |
| 6,461,378 B1 | 10/2002 | Knowlton | |
| 6,470,216 B1 | 10/2002 | Knowlton | |
| 6,858,571 B2 | 2/2005 | Pham et al. | |
| 7,006,874 B2 * | 2/2006 | Knowlton et al. | 607/101 |
| 7,022,121 B2 | 4/2006 | Stern et al. | |
| 7,091,388 B2 | 8/2006 | Tung et al. | |
| 7,098,176 B2 | 8/2006 | Singh et al. | |

(Continued)

FOREIGN PATENT DOCUMENTS

WO    9916502    4/1999

(Continued)

*Primary Examiner* — Kevin C Sirmons
*Assistant Examiner* — Andrew Gilbert
(74) *Attorney, Agent, or Firm* — Wood, Herron & Evans, LLP

(57) ABSTRACT

The present invention is directed to using cryogenic compositions, which are non-toxic, non-flammable, and have desirable ozone depletion and global warming potential, for cooling heated skin during skin treatments with a skin treatment apparatus.

8 Claims, 2 Drawing Sheets

U.S. PATENT DOCUMENTS

| | | | |
|---|---|---|---|
| 7,115,123 B2 | 10/2006 | Knowlton et al. | |
| 7,141,049 B2 | 11/2006 | Stern et al. | |
| 7,189,230 B2 | 3/2007 | Knowlton | |
| D544,955 S | 6/2007 | Carson et al. | |
| 7,229,436 B2 | 6/2007 | Stern et al. | |
| 7,257,450 B2 | 8/2007 | Auth et al. | |
| 7,267,675 B2 | 9/2007 | Stern et al. | |
| 7,452,358 B2 | 11/2008 | Stern et al. | |
| 7,473,251 B2 | 1/2009 | Knowlton et al. | |
| 7,473,252 B2 | 1/2009 | Barry | |
| 7,481,809 B2 | 1/2009 | Stern et al. | |
| 7,494,488 B2 | 2/2009 | Weber | |
| 7,569,170 B2 * | 8/2009 | Minor | 264/53 |
| 2004/0127383 A1 * | 7/2004 | Pham et al. | 510/412 |
| 2005/0233932 A1 | 10/2005 | Singh et al. | |
| 2005/0233933 A1 | 10/2005 | Singh et al. | |
| 2005/0245421 A1 | 11/2005 | Singh et al. | |
| 2006/0019857 A1 | 1/2006 | Wilson et al. | |
| 2006/0022166 A1 * | 2/2006 | Wilson et al. | 252/68 |
| 2006/0025322 A1 | 2/2006 | Wilson et al. | |
| 2006/0243945 A1 | 11/2006 | Minor et al. | |
| 2007/0088413 A1 | 4/2007 | Weber et al. | |
| 2008/0051612 A1 * | 2/2008 | Knapp et al. | 570/178 |

FOREIGN PATENT DOCUMENTS

| | | |
|---|---|---|
| WO | 0053113 | 9/2000 |
| WO | 0100269 | 1/2001 |
| WO | 03053266 | 3/2003 |
| WO | 03065915 | 8/2003 |
| WO | 03065916 | 8/2003 |
| WO | 03086217 | 10/2003 |
| WO | 2004086943 | 10/2004 |
| WO | 2004087253 | 10/2004 |
| WO | 2004088700 | 10/2004 |
| WO | 2004089185 | 10/2004 |
| WO | 2004089186 | 10/2004 |
| WO | 2004089459 | 10/2004 |
| WO | 2004089460 | 10/2004 |
| WO | 2004090939 | 10/2004 |
| WO | 2004105861 | 12/2004 |

* cited by examiner

METHOD OF USING CRYOGENIC COMPOSITIONS FOR COOLING HEATED SKIN

CROSS-REFERENCE TO RELATED APPLICATIONS

This application claims the benefit of U.S. Provisional Application No. 60/972,873, filed Sep. 17, 2007, which is hereby incorporated by reference herein in its entirely.

TECHNICAL FIELD

The present invention is directed to using cryogenic compositions, which are non-toxic, non-flammable, and have desirable ozone depletion and global warming potential, for cooling heated skin during skin treatments with a skin treatment apparatus.

BACKGROUND

Devices that can treat tissue non-invasively are extensively used to treat numerous diverse skin conditions. Among other uses, non-invasive energy delivery devices may be used to tighten loose skin to make a patient appear younger, remove wrinkles and fine lines, contour the skin, remove skin spots or hair, or kill bacteria. Such non-invasive energy delivery devices emit electromagnetic energy in different regions of the electromagnetic spectrum for tissue treatment. High frequency treatment devices, such as RF-based devices, may be used to treat skin tissue non-ablatively and non-invasively by passing high frequency energy through a surface of the skin, while actively cooling the skin to prevent damage to a skin epidermis layer.

Modern high frequency skin treatment apparatuses employ multiple discrete temperature sensors whose sensor packages are mounted on and attached to an electrode assembly for ostensively monitoring the temperature of the treatment tip of the high frequency device. Conventional high frequency capacitive electrodes consist of a pattern of metallic features carried on a flexible electrically insulating substrate, such as a thin film of polyimide. Despite being separated from the skin by the intervening insulating substrate, the temperature readings of the treatment tip measured by the thermistors is representative of the actual skin temperature. The insulating substrate is a poor conductor of heat.

The non-patient side of the electrode in the electrode assembly in the treatment tip, on which the thermistors are conventionally situated, may be sprayed with a coolant or cryogenic composition under feedback control of the thermistors for cooling the skin contacting the electrode assembly. The controller triggers the cryogenic composition based upon an evaluation of the temperature readings from the thermistors. The temperature readings from the thermistors are dependent upon, among other factors, the spray pattern of the cryogenic composition, any pooling of the cryogenic composition near or over the thermistor, and the evaporation rate of any cryogenic composition wetting the thermistor, for example.

Chlorofluorocarbons (CFCs), hydrochlorofluorocarbons (HCFCs), and/or mixtures containing these compounds have conventionally been used as the cryogenic composition. However, because of their high chlorine content, chemical stability, and long atmospheric lifetimes, such compounds, when released to the atmosphere, can migrate to the stratosphere where they undergo photolysis and deplete the earth's protective ozone layer. CFCs particularly contribute to depletion of the ozone layer, with the HCFCs depleting the ozone layer to a lesser extent. As a result, production of CFCs and HCFCs has been and continues to be severely limited and is scheduled for phase out in many industrialized and non-industrialized countries.

Accordingly, the industry is continually seeking new fluorocarbon based mixtures that offer alternatives, and are considered environmentally safer substitutes for CFCs and HCFCs. Of particular interest are mixtures containing hydrofluorocarbons that are nonflammable, non-toxic and environmentally benign in having zero ozone depletion potentials, low global warming potentials (less than about 150) and negligible atmospheric and terrestrial environmental impacts. One currently used cryogenic composition is 1,1,1,2-tetrafluoroethane (R-134a). However, this cryogenic composition has significant and undesirable global warming potential (GWP=1410).

Accordingly, a need exists to use cryogenic compositions that can be used as efficient and economical substitutes for CFC and/or HCFCs. A need still exists for developing cryogenic compositions with a particular combination of properties for more specific applications. For example, suitable replacements for CFCs, HCFCs and/or hydrofluorocarbons (HFCs) must be non-flammable, non-toxic, and unreactive and provide a desirable or low global warming potential, i.e., a GWP of less than about 150. Further, in order for a cryogenic composition to adequately serve as a replacement for CFCs, HCFCs and/or HFCs, the substitute cryogenic compositions must be effective under the same operating conditions thereby serving as "drop in" replacements for CFCs, HCFCs and/or HFCs or "near drop in" replacements for such materials. In view of this combination of necessary properties, a need still exists for further development of suitable replacement materials, particularly for skin cooling during skin treatments.

SUMMARY OF THE INVENTION

In accordance with one embodiment, a method for treating tissue located beneath a skin surface includes positioning an electrode of a skin treatment apparatus adjacent to a skin surface. The skin treatment apparatus is adapted to deliver energy via the electrode to tissue located beneath the skin surface by applying energy to tissue located beneath the skin surface via the electrode. Spraying a cryogenic composition against a non-patient side of the electrode cools the patient's skin. The cryogenic composition includes one of the following: (a) 1,1,3,3,3-pentafluoropropene, 1,2,3,3,3-pentafluoropropene, or mixtures thereof; (b) 1,3,3,3-tetrafluoropropene alone or in combination with trifluoroiodomethane, 1,1,3,3,3-pentafluoropropene, or 1,2,3,3,3-pentafluoropropene; (c) 2,3,3,3-tetrafluoropropene alone or in combination with trifluoroiodomethane, 1,1,3,3,3-pentafluoropropene, or 1,2,3,3,3-pentafluoropropene; (d) 1,1-difluoroethane in combination with 1,1,3,3,3-pentafluoropropene, 1,2,3,3,3-pentafluoropropene, or trifluoroiodomethane; (e) 3,3,3-trifluoropropene in combination with 1,1,3,3,3-pentafluoropropene, 1,2,3,3,3-pentafluoropropene, or trifluoroiodomethane; (f) trifluoroiodomethane alone or in combination with 1,1,3,3,3-pentafluoropropene, or 1,2,3,3,3-pentafluoropropene; or (g) propyne in combination with 1,1,3,3,3-pentafluoropropene, 1,2,3,3,3-pentafluoropropene, or trifluoroiodomethane.

BRIEF DESCRIPTION OF THE DRAWINGS

The accompanying drawings, which are incorporated in and constitute a part of this specification, illustrate embodi

DETAILED DESCRIPTION OF SPECIFIC EMBODIMENTS

The overall purpose of this effort is to find one or more attractive low-global-warming cryogenic fluid(s) to replace 1,1,1,2-tetrafluoroethane (R-134a) in a skin treatment apparatus. The requirements include nonflammability under normal circumstances, low toxicity, acceptable cost, boiling point within 10° C. of the boiling point of R-134a (which is −26° C., so the desired range is −16° C. to −36° C.), acceptable compatibility with materials of construction, zero ozone-depletion potential (ODP) and global warming potential (GWP) below 140 (to conform to European import requirements). The present invention is comprised of combinations of cryogens that can meet the above requirements and a skin treatment apparatus for delivering high frequency energy to the skin of a subject, which utilizes the cryogenic compositions.

Figure 1:
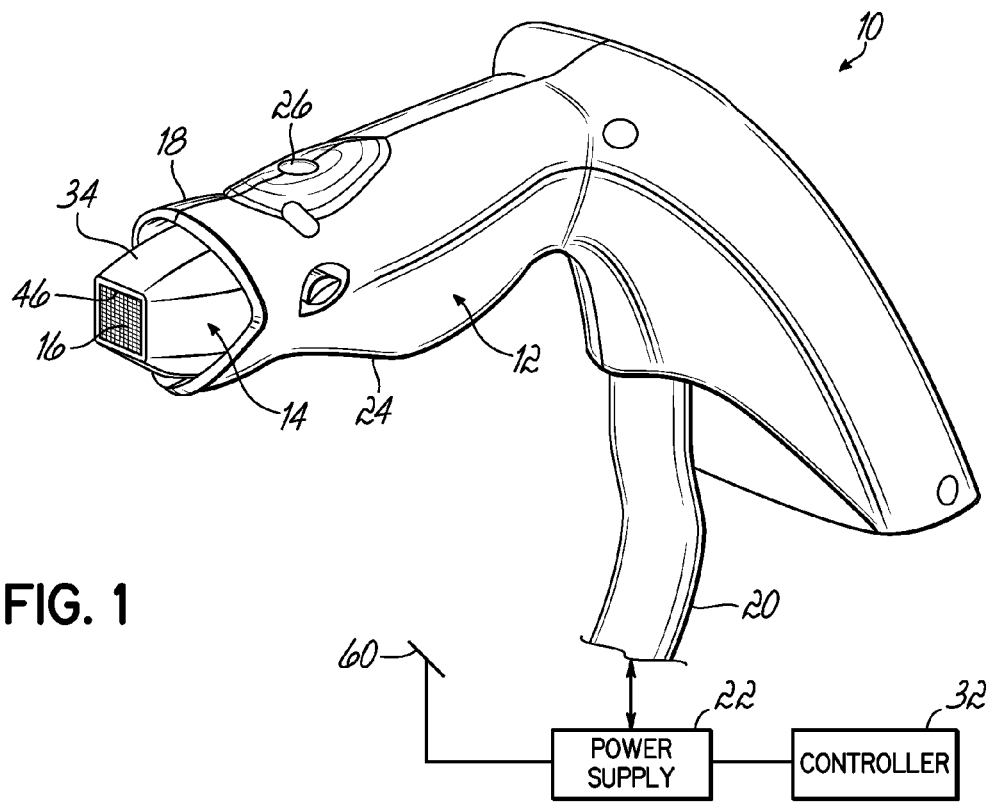
- FIG. 1 is a perspective view of a handpiece including an electrode assembly in accordance with an embodiment of the present invention.

Briefly, with reference to FIG. 1, a skin treatment apparatus or handpiece 10 includes a housing 12 typically composed of a plastic or polymer material, such as a cured polymer resin, that is molded, such as by an injection molding process, into a three-dimensional shape. Releasably coupled with the housing 12 is an electrode structure or assembly 14 (i.e., treatment tip) having a leading end carrying an electrode 16, which protrudes from a shroud 18 defined at one end of the housing 12. When the electrode assembly 14 is coupled mechanically with the housing 12, the electrode 16 is exposed and visible.

Housing 12 provides a suitable interface for connection to an electrical connecting cable 20 that includes insulated and shielded conductors or wires (not shown) that electrically couple the electrode assembly 14 with a high frequency electromagnetic generator or power supply 22. Electrical connections (discussed below) inside a hollow interior of the housing 12 electrically couple the electrode assembly 14 with the high frequency power supply 22, which supplies high frequency current to the electrode 16 carried by electrode assembly 14.

Handpiece 10 includes a smoothly contoured grip portion 24 having a shape suitable for gripping and handling by the clinician. The grip portion 24 is adapted to be grasped by at least one hand of the clinician for manipulating the handpiece 10 to maneuver the electrode assembly 14 to a location proximate to a patient's skin. Preferably, the electrode 16 of electrode assembly 14 is in contact with a skin surface. A target tissue for the high frequency electromagnetic energy radiated from the electrode 16 lies beneath the skin surface. The target tissue is typically the dermis of the patient's skin and the epidermis of the patient's skin is disposed between the target tissue and the skin surface. An activation button 26 is depressed and released for actuating a switch that controls the delivery of high frequency energy from the electrode 16 to treat the target tissue.

An electrical circuit (not shown) in the high frequency power supply 22 is operative to generate high frequency electrical current, typically in the radio-frequency (RF) region of the electromagnetic spectrum, which is transferred to the electrode 16. The operating frequency of power supply 22 may advantageously be in the range of several hundred KHz to about 20 MHz to impart a therapeutic effect to the tissue. The power supply circuit converts a line voltage into drive signals having an energy content and duty cycle appropriate for the amount of power and the mode of operation that have been selected by the clinician, as understood by a person having ordinary skill in the art. High frequency energy is delivered to the patient's skin and underlying tissue over a short delivery cycle (e.g., about 1 second to about 10 seconds), after which the handpiece 10 is manipulated to position the electrode assembly 14 near a different region of the skin surface for another treatment cycle of high frequency energy delivery.

A controller 32 is used to control the operation of the high frequency power supply 22. The controller 32 may include user input devices to, for example, adjust the applied voltage level of high frequency power supply 22 or switch between different modes of operation. The controller 32 includes a processor, which may be any suitable conventional microprocessor, microcontroller or digital signal processor, that controls and supervises the operation of the power supply 22 for regulating the power delivered from the power supply 22 to the electrode 16. Controller 32 may also include a nonvolatile memory (not shown) containing programmed instructions for the processor and may be optionally integrated into the power supply 22.

Figure 2:
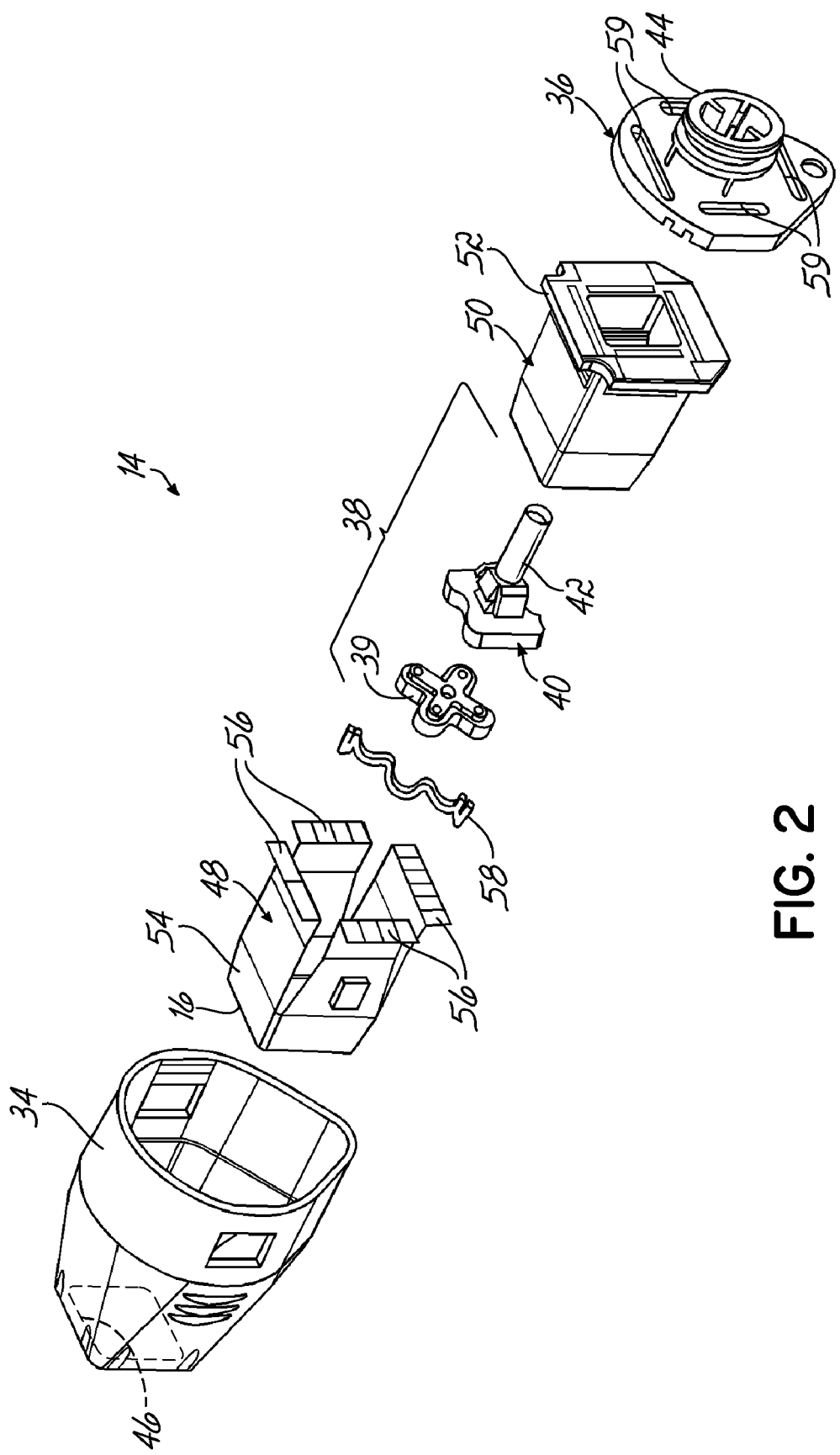
FIG. 2 is an enlarged view of the electrode assembly of FIG. 1.

With reference to FIGS. 1 and 2, the electrode assembly 14 includes an outer shell 34 and a nipple 36 that is coupled with the open rearward end of the outer shell 34 to surround an interior cavity. A fluid delivery member 38 is configured to deliver a spray of a cryogenic composition from a nozzle 39 for controlling the temperature of the electrode 16. Extending rearwardly from a central fluid coupling member 40 is a conduit 42 having a lumen defining a fluid path that conveys a flow of the coolant to the nozzle 39. The coolant is pumped from a coolant supply (not shown) through tubing that is mechanically coupled with a fitting 44 formed on the nipple 36 and hydraulically coupled with the lumen of the conduit 42.

One purpose of the cryogenic composition is to pre-cool the patient's epidermis, before powering the electrode 16, by heat transfer between the electrode assembly 14 and a portion of the tissue, typically the patient's epidermis. As a result, the high frequency energy delivered to the tissue fails to heat the epidermis to a temperature sufficient to cause significant epidermal thermal damage. Depths of tissue that are not significantly cooled by pre-cooling will warm up to therapeutic temperatures resulting in the desired therapeutic effect. The amount or duration of pre-cooling may be used to select the protected depth of untreated tissue. The cryogenic composition may also be used to cool portions of the tissue during and/or after heating by the transferred high frequency energy. Various duty cycles of cooling and heating by high frequency energy transfer are utilized depending on the type of treatment and the desired type of therapeutic effect. The cooling and heating duty cycles may be controlled and coordinated by operation of the controller 32.

The electrode 16 is exposed through a window 46 defined in a forward open end of the outer shell 34. The electrode 16 may be formed as a conductive feature on a substrate 48 (FIG. 2), which in the representative embodiment of the present invention is a flexible sheet of dielectric material wrapped about a forward end of a support member 50. The rearward end of the support member 50 includes a flange 52 used to couple the support member 50 to the nipple 36. The flexible substrate 48 may comprise a thin base polymer (e.g., polyimide) film 54 and may include thin conductive (e.g., copper) traces or leads 56 isolated electrically from each other by small intervening gaps. Flexible substrate 48 may comprise a flex circuit having a patterned conductive (i.e., copper) foil laminated to a base polymer (or other non-conductive material) film or patterned conductive (i.e., copper) metallization layers directly deposited on a base polymer film by, for example, a vacuum deposition technique, such as sputter deposition. Flex circuits, which are commonly used for flexible and high-density electronic interconnection applications, have a construction understood by a person having ordinary skill in the art. A support arm 58 bridges the window 46 for lending mechanical support to the flexible substrate 48.

The flexible substrate 48 is wrapped or folded about the support member 50 such that the conductive leads 56 are exposed through slots 59 defined in the nipple 36. The conductive leads 56 couple the electrode 16 with the high frequency power supply 22. The conductive leads 56 may also be used to couple other structures, such as impedance or pressure sensors (not shown), with the controller 32 of high frequency power supply 22 or another control element either inside the housing 12 or external to the housing 12.

A non-therapeutic passive or return electrode 60 (FIG. 1) is attached to a body surface of the patient that is not being treated (i.e., the patient's back) and is electrically coupled with a negative voltage polarity terminal of the high frequency power supply 22. During treatment, high frequency current flows through the bulk of the patient between the handpiece 10 and the return electrode 60 in a closed circuit. Current delivered by the handpiece 10 is returned to the high frequency power supply 22 from the return electrode 60, after having been conducted through the target tissue of the patient. Because of the low current density delivered across the relatively large area of the return electrode 60, the return electrode 60 is non-therapeutic in that no significant heating is produced at its attachment site to the patient's body. A suitable treatment handpiece is shown and described in commonly-assigned U.S. Application No. 60/728,339, entitled "Treatment Apparatus Having Multiple Selectable Depths of Energy Delivery" and filed on Oct. 19, 2005, and in commonly assigned U.S. application Ser. No. 11/423,068, filed on Jun. 8, 2006 and published on Apr. 19, 2007 as Publication No. 2007/0088413, the disclosures of which are hereby incorporated by reference herein in their entirety.

The cryogenic compositions for use with the skin treatment apparatus of the present invention include 1,1,3,3,3-pentafluoropropene, 1,2,3,3,3-pentafluoropropene, 1,3,3,3-tetrafluoropropene, 2,3,3,3-tetrafluoropropene, trifluoroiodomethane, propyne, 1,1-difluroethane, and 3,3,3-trifluoropropene. These cryogens can be used as a refrigerant in the skin treatment apparatus in either their pure form or in blends of two or more cryogens.

It has been determined that cryogenic compositions comprising blends of these compounds are particularly advantageous for use in refrigeration applications. The cryogenic compositions are nonflammable and are azeotropic or near azeotropic, whereby the cryogenic compositions are physically stable and do not substantially fractionate during use. Within the context of the invention, near-azeotropic cryogenic compositions are those in which the difference in vapor pressures of the components at room temperature is less than 10 psi. Accordingly, the cryogenic compositions, which consist essentially of the recited components in the various embodiments, exclude components which would render the cryogenic compositions flammable and/or render the cryogenic compositions non-azeotropic or non-near azeotropic, thereby causing the cryogenic compositions to exhibit substantial fractionation among the components The cryogenic compositions are particularly suitable for use in methods for providing refrigeration wherein a refrigerating amount of a cryogenic composition is provided in a cooling system and the cooling system is operated to provide refrigeration. As is well known in the refrigeration art, extensive refrigeration and air conditioning equipment conventionally designed for use with CFCs and/or HCFCs is currently in existence. The cryogenic compositions are particularly suitable for use as replacements for the CFCs and/or HCFCs, and are suitable for use with the pre-existing equipment under normal operating conditions. The present cryogenic compositions are also suitable replacements for pure HFC cryogenic compositions. For example, the cryogenic compositions can be used as suitable replacements for HFC134a and provide higher energy efficiency and capacity, a significantly decreased global warming potential (decreased by almost two thirds), and significantly decreased total equivalent warming impact (TEWI).

The cryogenic compositions are suitable for use in refrigeration systems operating over conventional temperature ranges, and over wider temperature ranges, if necessary. The cryogenic compositions according to the invention are also particularly suitable for use in methods for providing refrigeration in view of their refrigeration performance properties, physical stability, electrical non-conductivity, low toxicity, non-flammability (self-extinguishing), short atmospheric lifetime, zero ozone depletion potential, low global warming potential, and negligible terrestrial environmental impact. Thus, the cryogenic compositions are suitable replacements for various conventional CFC and HCFC refrigerants. Also, the present cryogenic compositions are suitable for use as low global warming and low-TEWI (total equivalent warming impact) replacements for HFC134a.

The components of the cryogenic compositions of the invention may be manufactured according to known techniques and are all commercially available. Additionally, the blends of cryogenic compositions according to the invention are prepared by simple blending of the components in accordance with conventional techniques, or in accordance with other methods known in the art.

In general, pure chemicals are simpler to handle than blends. Blends require mixing, may fractionate on evaporation, and materials in contact with a blend must be compatible with all components in order to be compatible with a blend. However, sometimes by using blends it is possible to achieve better properties for a particular use and lower cost than with a single chemical.

Because they are less complex molecules, flammable components are often less expensive and less toxic than nonflammable components. For these reasons it is desirable to find nonflammable blends that minimize the quantities of nonflammable components required. The purpose of this effort was to find suitable low-GWP blends minimizing the quantities of nonflammable components needed.

Described here are the results of flammability tests to determine non-flammable binary (two-component) mixtures. The mixtures contained either 1,1,3,3,3-pentafluoropropene or trifluoroiodomethane ($CF_3I$) as the non-flammable component, and the flammable component was selected from the set consisting of a tetrafluoropropene (either 1,3,3,3- or 2,3,3,3-), trifluoropropene, 1,1-difluroethane (R-152a), or propyne. Table 1 below lists the pairs that were investigated in this effort, each consisting of one of the two non-flammable components plus one of the five flammable components. Two of the blends have already been developed. One of these is Honeywell's H-Fluid, consisting of a blend of 2,3,3,3-tetrafluoropropene plus $CF_3I$. The other is the Environmental Technology & Engineering Center's (ETEC) Ikon A blend, consisting of $CF_3I$ and R-152a. Blends were tested to determine how much of the non-flammable component is needed to render the blend non-flammable at room temperature according to ASTM E-681.

TABLE 1

Binary blends considered for cryogenic compositions

| | | | Flammable component | | |
|---|---|---|---|---|---|
| Nonflammable component | R-152a | propyne | 1,3,3,3-tetrafluoropropene | 2,3,3,3-tetrafluoropropene | 3,3,3-trifluoropropene |
| 1,1,3,3,3-pentafluoropropene | Tested | Tested | Tested | Tested | Tested |
| CF$_3$I | Ikon A Not Tested | Tested | Not Tested | Honeywell H-fluid Tested | Tested |

It was determined that the most promising chemical family for new cryogens is the fluorinated propenes. This family of compounds has attractive physical properties, appears to have low toxicity, and has zero ODP and very low GWPs. Propenes are three-carbon molecules containing a double bond, and the fluoropropenes of interest include pentafluoropropenes, tetrafluoropropenes and trifluoropropenes.

Both pentafluoropropene and tetrafluoropropene exist in several isomeric structures. In general, isomers are expected to have similar flammability properties. Currently, all isomers of pentafluoropropene and tetrafluoropropene are only made in small quantities and are quite expensive.

Three isomers of pentafluoropropene are known. Two have boiling points within the proper range for consideration as potential cryogens. These are 1,1,3,3,3-pentafluoropropene (bp −21° C.) and 1,2,3,3,3-pentafluoropropene (bp −18° C.). The third isomer, 1,1,2,3,3-pentafluoropropene, boils at about 1° C., outside the acceptable range for a replacement cryogen. All the pentafluoropropenes are reported to be non-flammable when tested at 100° C. Of the two pentafluoropropenes with appropriate volatility, the one easiest to manufacture is the 1,1,3,3,3 isomer.

1,2,3,3,3-pentafluoropropene was not tested, though it would be expected that this isomer would perform similarly to 1,1,3,3,3-pentafluoropropene.

Chemicals with two or more substituents on a double bond can exist in isomeric forms, differing in which side of the double bond the substituents are on. These isomers are called E (for the German entgegen, opposite) and Z (for the German zusammen, together). E and Z correspond to trans and cis isomers when only two substituents are involved. The 1,2,3,3-pentafluoropropene is available as a mixture of E and Z isomers (CAS number 2252-83-7). It is also available as the pure Z isomer (CAS number 5528-43-8).

Three isomers of tetrafluoropropene are known. The two more common and available are 1,3,3,3-(bp −16° C.) and 2,3,3,3-(bp −28° C.). Of these, the 2,3,3,3 has a more attractive boiling point to avoid pooling of cryogen during evaporations. These two isomers of tetrafluoropropene are reported to be flammable at 100° C,. and 3,3,3-trifluoropropene is also flammable at 100° C. For this effort, both of the more common isomers of tetrafluoropropene were tested.

It appears that either the 1,1,3,3,3 or 1,2,3,3,3 isomer of pentafluoropropene in pure form could be an acceptable replacement for R-134a as a coolant for a skin treatment apparatus. If it is desired to use a tetrafluoropropene or trifluoropropene, then these should be blended with a non-flammable component to eliminate flammability in the blend.

Because of the long chemical names involved, abbreviations are sometimes used in this specification. Penta is used to designate 1,1,3,3,3-pentafluoropropene because that is the only isomer of pentafluoropropene tested for this effort; 1-tetra means 1,3,3,3-tetrafluoropropene; 2-tetra means 2,3,3,3-tetrafluoropropene; and tri means 3,3,3-trifluoropropene.

In addition to fluorinated propenes, three other chemicals with appropriate physical and environmental characteristics were considered. One of these is trifluoromethyl iodide (CF$_3$I). This chemical is non-flammable, boils at −23° C., and has zero ODP and an extremely low GWP (about 6). However, toxicity studies have revealed that if inhaled in high concentrations it can cause cardiac sensitization to adrenaline in beagle dogs. Therefore, it has been recommended that people should not be exposed to more than 2,000 ppm for brief periods (the EPA recommended short-term exposure limit, STEL) or more than 150 ppm consistently over a working lifetime (the EPA recommended acceptable exposure limit, AEL) (see "Review of the Components of the Ikon Refrigerant Blends and Recommendations for Acceptable Exposure Limits (AELs)," Environ Corp., March 1998).

Because of the cardiac sensitization risk, for example, trifluoromethyl iodide is considered less attractive than other components.

Another component considered is R-152a (HFC-152a, 1,1-difluoroethane). This chemical has been produced in bulk for several years, has very low toxicity, boiling point of −25° C., zero ODP, GWP of 140, and is available at a low cost. Its only drawback is that it is highly flammable and therefore would have to be blended with a non-flammable component.

Propyne (methylacetylene) was also considered as a possible blend component. It is highly flammable, but has an attractive boiling point of −23° C., zero ODP and near-zero GWP.

Table 2 below lists properties of components considered for custom cryogen blends for use in a skin treatment apparatus.

TABLE 2

Blend components and the commercial blends considered for cryogenic compositions.

| Chemical | BP, ° C. | Composition | HFC Number | CAS No. | Attractiveness & Comments |
|---|---|---|---|---|---|
| 1,1-difluoroethane (R-152a) | −25 | CHF$_2$CH$_3$ | 152a | 75-37-6 | High but very flammable |

TABLE 2-continued

Blend components and the commercial blends considered for cryogenic compositions.

| Chemical | BP, °C. | Composition | HFC Number | CAS No. | Attractiveness & Comments |
|---|---|---|---|---|---|
| 1,1,3,3,3-pentafluoropropene | −21 | $CF_2$=CH—$CF_3$ | 1225zc | 690-27-7 | High if toxicity and cost acceptable |
| ez 1,2,3,3,3-pentafluoropropene | −18 | CHF=CF—$CF_3$ | 1225ye | 2252-83-7 | High if toxicity and cost acceptable |
| 1,3,3,3-tetrafluoropropene | −16 | CHF=CH—$CF_3$ | 1234ze | 1645-83-6 | High if toxicity and cost acceptable |
| 2,3,3,3-tetrafluoropropene | −28 | $CH_2$=CF—$CF_3$ | 1234yf | 754-12-1 | High if toxicity and cost acceptable |
| 3,3,3-trifluoropropene | −17 | $CH_2$=CH—$CF_3$ | 1243zf | 677-21-4 | High if toxicity and cost acceptable |
| propyne (methylacetylene) | −23 | HC≡C—$CH_3$ | NA | 74-99-7 | Moderate - expensive and extremely flammable |
| Trifluoromethyl iodide | −23 | $CF_3I$ | 13I1 | 2314-97-8 | Low (cardiac sensitization risk) |
| Unnamed Patented Blend | −24 | Blend of pentafluoropropene and tetrafluoropropene | Not publicly known | Not publicly known | High |
| ETEC'S Ikon A blend | −24 | Blend of trifluoromethyl iodide + 1,1-difluoroethane (R-152a) | 13I1 + 152a | 2314-97-8 + 75-37-6 | Low (cardiac sensitization risk) |

Procedure

Flammability tests of gases and gas blends were conducted based on the procedures in ASTM E-681 "Standard Test Method for Concentration Limits of Flammability of Chemicals (Vapors and Gases)." This method for determining the lower flammability limit (LFL) of refrigerant gases has been previously described (see D. P. Wilson and R. G. Richard, "Determination of Refrigerant Lower Flammability Limits in Compliance with Proposed Addendum p to Standard 34," ASHRAE Transactions 2002, Vol. 108, part 2, pp. 739-756, which is hereby incorporated by reference herein in its entirety). The flammability apparatus used for this testing is conventional and known in the art.

In this test, the desired gases are blended then the desired concentration of the blend is introduced into a 12-liter flask, mixed with air at 50% relative humidity, stirred, and allowed to equilibrate. In order to maintain relative humidity near 50%, air passing into the flask first passes through a "double-bucket" system consisting of two large flasks containing saturated solutions of calcium nitrate in distilled water. This automatically provides air at about 50% relative humidity.

A video camera is turned on to record any flames generated in the flask and to allow playback in case tests near the borderline of flammability need to be reviewed. The mixture is then sparked up to three times using a 15 KV, 30 mA spark for 0.4 seconds. The results are recorded as one of the following: spark only, a flame reaching one to eight inches above the electrodes, or a flame filling ⅛ flask, ¼ flask, ⅓ flask, ½ flask, or the whole flask. As defined in the test, the flammability borderline occurs at ¼ flask, and positive flammability is anything more than ¼ flask. This region is marked with narrow tape on the flask as an inverted cone with sides running upward at 45° on both sides from the tip at the electrodes. If a flame extends outside this 90° (¼ flask) zone, the test is considered positive and therefore the mixture is considered flammable.

It should be noted that ASTM E-681 is a very severe flammability test. Substances which do not show flammability in numerous other tests can show flammability in this test. For example, trichloroethylene and tetrachloroethylene (perchloroethylene, dry cleaning fluid) are nonflammable by all standard solvent flammability tests and have been used for decades in million-pound quantities without any flammability problems. These solvents, though, when tested by ASTM E-681, show positive flammability.

This test can be run at temperatures ranging from room temperature to 100° C. The tests were conducted at room temperature as being the most representative of the conditions to be experienced by the cryogen. Generally, the higher the temperature, the greater the flammability observed.

According to the American Society of Heating, Refrigeration, and Air-Conditioning Engineers (ASHRAE), to be classified as nonflammable, refrigerants must pass the ASTM E-681 flammability test at 100° C. This is because refrigerant gases can be exposed to high temperatures, for example at the compressor discharge in a refrigeration system. In a skin treatment apparatus, the cryogen gas is not exposed to high temperatures or significant ignition sources. Thus, determining non-flammability by ASTM E-681 at room temperature provides an adequate margin of safety for use in skin treatment apparatus.

It should also be kept in mind that these tests were conducted at ambient atmospheric pressure in Albuquerque, N. Mex., at an elevation of about 5000 ft. At this elevation ambient pressure is about 630 torr. It would be expected that tests conducted near sea level (at about 760 torr) would show somewhat greater flammability because the oxygen concentration would be higher.

For each pair tested, an initial estimate was made of the ratio that might be near the flammability borderline. This blend was mixed and tested at about 8-12 different concentrations in air. For each test in a given series, the ratio of the nonflammable to flammable component remains the same but the concentrations of each in air change because of differing dilutions. If any test point (dilution) in a series at a given ratio of components tests flammable, that ratio is considered flammable. Special attention was given to finding the flammability borderlines. This is the place where the test results change from ¼ flask (negative) to ¼ flask (positive).

If flammability was observed at any concentration, another blend was made using a higher ratio of the nonflammable component, and then another series of tests was conducted at different dilutions in air. Conversely, if the first series showed no flammability, the proportion of nonflammable component was increased and another series was run. If the series seemed far from a borderline (i.e., very great or no flammability), the ratio for the next run was changed by 10%. Once the ratio was bracketed with a nonflammable and flammable series, the ratio was narrowed down by progressive changes in component ratios of 5% or 2.5%. For each pair, about 20 to 50 individual flammability tests are required to create a flammability diagram and establish the ratio required for nonflammability. In this study, for the pairs tested, about 320 individual flammability tests were conducted.

Figure 3:
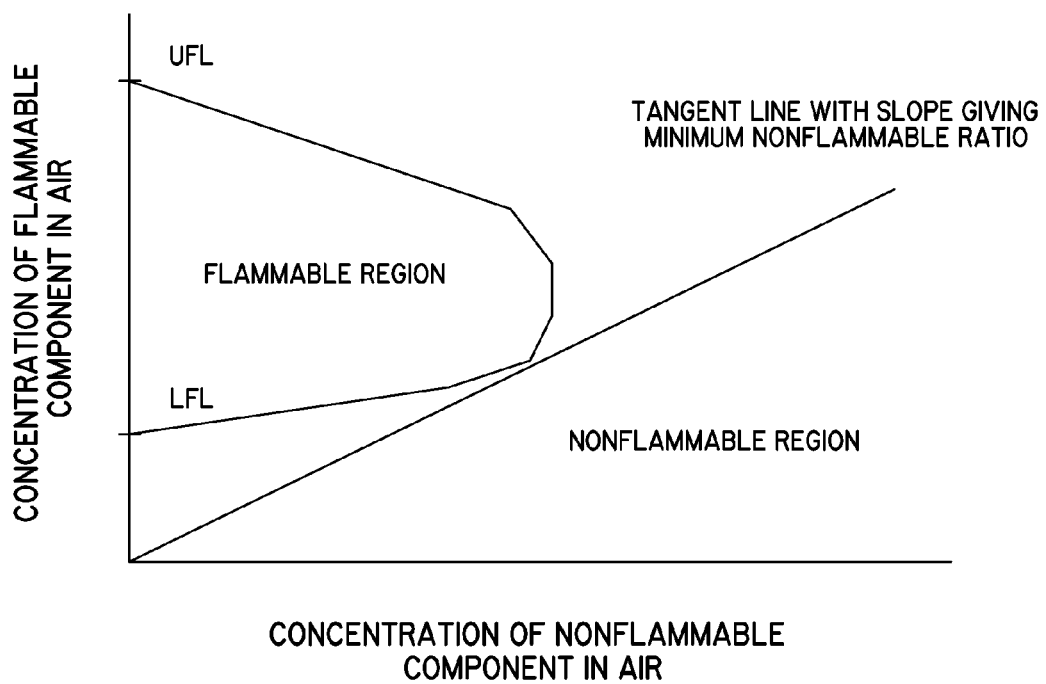
FIG. 3 is a flammability diagram for a blend of a flammable and nonflammable component.

If the concentration in air of the nonflammable component is plotted along the X-axis and the concentration in air of the flammable component is plotted along the Y-axis, a flammability diagram is obtained. A series of dilutions of the same ratio forms a series of points along a line from the origin. Each point is marked positive (flammable) or negative (nonflammable) on the diagram. A region of flammability is then defined, stretching from the lower flammability limit (LFL) of the flammable component on the bottom in a nosecone-shaped region up to the upper flammability limit (UFL) of the flammable component. Once this region is defined, a tangent line can be drawn from the origin to the lower boundary of this region, and the slope of this tangent line defines the ratio of the two components that is never flammable at any dilution in air. This is illustrated in FIG. 3.

Test Results

For various blends of chemicals, as further discussed below, a total of about 320 individual flammability tests were conducted. For each pair of components, each ratio was tested in different air concentrations. A flammability observation was made and whether each test was positive or negative. From these tests, nonflammable blends were identified. The nonflammable blends identified are listed in Table 3 below. Each blend will be discussed in turn below, after a brief discussion of fractionation.

TABLE 3

Nonflammable cryogenic compositions

| Nonflammable component | Flammable component | Flammability Borderline % Nonflam by moles | % Flam by moles | Mixture allowing 5% fractionation | | | | Comments |
| --- | --- | --- | --- | --- | --- | --- | --- | --- |
| | | | | % Nonflam by moles | % flam by moles | % Nonflam by wt | % Flam by wt | |
| 1,1,3,3,3-pentafluoropropene | 1,3,3,3-tetra | 0% | 100% | 5% | 95% | 6% | 94% | Attractive |
| 1,1,3,3,3-pentafluoropropene | R-152a | 65% | 35% | 70% | 30% | 82% | 18% | Might lower cost of penta |
| 1,1,3,3,3-pentafluoropropene | 2,3,3,3-tetra | 10% | 90% | 15% | 85% | 17% | 83% | Attractive |
| 1,1,3,3,3-pentafluoropropene | propyne | 83% | 17% | 88% | 12% | 96% | 4% | Not attractive-propyne too flammable |
| 1,1,3,3,3-pentafluoropropene | tri | 50% | 50% | 55% | 45% | 63% | 37% | Might lower cost of penta |
| $CF_3I$ | 2,3,3,3-tetra | 9% | 91% | 14% | 86% | 22% | 78% | Blend with lowest % $CF_3I$, better than H-Fluid or Ikon A |
| $CF_3I$ | propyne | 92% | 8% | 97% | 3% | 99% | 1% | Not attractive-propyne too flammable |
| $CF_3I$ | tri | 37% | 63% | 42% | 58% | 50% | 50% | Blend with lower % $CF_3I$ than H-Fluid or Ikon A |

Fractionation

If a mixture evaporates slowly, for example from a slow leak, the cryogenic composition of the mixture changes during the evaporation. The first vapor to escape is enriched in the more volatile component, and the final vapor is enriched in the less volatile component. This could pose a potential flammability risk if the flammable component is evaporating and not enough of the nonflammable component is present in the vapor to inhibit combustion.

All of the components considered for cryogen blends in this effort have very similar volatilities so are not expected to fractionate greatly. Previous studies have shown that mixtures in this volatility range have fractionated generally on the order of 5%. In other words, the change in cryogenic composition from first to last vapor is about 5%. This level of fractionation has been accounted for by adding an extra 5% of the nonflammable component. If it becomes clear that a particular blend is especially attractive and it is desired to commercialize it, it would be highly advisable to conduct actual fractionation tests on that blend to make sure that a flammable cryogenic composition never forms. To ensure nonflammability, it may be necessary to increase the proportion of the nonflammable component by up to another 5%.

Fractionation tests can be conducted according to standard procedures described in UL Standard 2182 and ASHRAE Standard 34. These tests involve filling a cylinder with a blend, establishing a slow leak (2%/hr) through a flowmeter, and monitoring the cryogenic composition of the escaping gas blend by gas chromatography.

Discussion of Blends Tested 1,1,3,3,3-Pentafluoropropene and
3,3,3-Trifluoropropene (Penta/Tri)

This blend was tested at the following ratios by mole percent: 40/60, 45/55, and 50/50. Both the 40/60 and 45/55 blends had substantial ranges of flammability. The 50/50 blend had only one (1) concentration in air that tested flammable and this concentration showed the minimum possible positive flammability of one-quarter (¼) flask. Therefore, the borderline of flammability for this blend at room temperature is 50/50. Allowing for 5% changes in cryogenic composition due to fractionation, this gives a 55/45 blend as a possible cryogen. This corresponds to about 63% by weight of 1,1,3,3,3-pentafluoropropene and about 37% by weight of 3,3,3-trifluoropropene. In one example, the ratio by weight for non-flammability is about 63% to about 99% 1,1,3,3,3-pentafluropropene to about 1% to about 37% 3,3,3-trifluoropropene.

1,1,3,3,3-Pentafluoropropene and
2,3,3,3-Tetrafluoropropene (Penta/2-Tetra)

This blend was tested at the following ratios by mole percent: 10/90 and 0/100 (pure 2-tetra). The pure 2-tetra showed flammability between 7% and 13% in air at room temperature. The 10/90 blend had only one concentration in air that tested flammable and this concentration showed the minimum possible positive flammability of one-quarter flask. Therefore, the borderline of flammability for this blend at room temperature is 10/90. Allowing for 5% changes in cryogenic composition due to fractionation, this gives a 15/85 blend as a possible cryogen. This corresponds to about 17% by weight of 1,1,3,3,3-pentafluoropropene and about 83% by weight of 2,3,3,3-tetrafluoropropene. In one example, the ratio by weight for non-flammability is about 17% to about 99% 1,1,3,3,3-pentafluropropene to about 83% to about 1% 2,3,3,3-tetrafluoropropene. In another example, the ratio by weight for non-flammability is about 17% to about 50% 1,1,3,3,3-pentafluropropene to about 83% to about 50% 2,3,3,3-tetrafluoropropene.

1,1,3,3,3-Pentafluoropropene and R-152a
(Penta/152a)

This blend was tested at the following ratios by mole percent: 50/50, 60/40, 65/35, and 67.5/32.5. Both the 50/50 and 60/40 blends showed flammability at a wide range of concentrations of air at room temperature. The 65/35 blend had only one concentration in air that tested flammable and this concentration showed the minimum possible positive flammability of one-quarter flask. The 67.5/32.5 blend showed no flammability at any concentration in air. Therefore the borderline of flammability for this blend at room temperature is 65/35. Allowing for 5% changes in cryogenic composition due to fractionation, this gives a 70/30 blend as a possible cryogen. This corresponds to about 82% by weight of 1,1,3,3,3-pentafluoropropene and about 18% by weight of R-152a. In one example, the ratio by weight for non-flammability is about 82% to about 99% 1,1,3,3,3-pentafluoropropene to about 1% to about 18% R-152a. R-152a is already available in bulk at low cost (about $3.00/lb) and has been proven to have very low toxicity.

1,1,3,3,3-Pentafluoropropene and
1,3,3,3-Tetrafluoropropene (Penta/1-Tetra)

This blend was tested at the following ratios by mole percent: 30/70; 20/80; 10/90; 5/95 and 0/100 (pure 1-tetra). The reported LFL and UFL for 1-tetra at 100° C. are 5.0% and 14.5% (see B. Minor et al., "Compositions Comprising a Fluoroolefin," U.S. Patent Application Number 20060243945, Nov. 2, 2006, DuPont). When we performed these flammability tests at room temperature, all flammability tests were negative, even for the pure 1-tetra. The 1-tetra in pure form did give a marginally negative flammability results (¼ flask negative) over the range of 8% to 10% concentrations in air. In other words, under the conditions of our testing, pure 1-tetra was shown to be non-flammable by ASTM E-681 at room temperature. Therefore, we found that 1,3,3,3-tetrafluoropropene is much less flammable at room temperature than at 100 degrees C. It should be kept in mind that gases normally exhibit lower flammability at lower test temperatures. In one example, the ratio by weight for non-flammability is about 1% to about 50% 1,1,3,3,3-pentafluoropropene to about 50% to about 99% 1,3,3,3-tetrafluoropropene. In another example, the ratio by weight for non-flammability is about 1% to about 25% 1,1,3,3,3-pentafluropropene to about 75% to about 99% 1,3,3,3-tetrafluoropropene. In yet another example, the ratio by weight for non-flammability is about 5% 1,1,3,3,3-pentafluropropene to about 95% 1,3,3,3-tetrafluoropropene.

In summary, 1-tetra tests marginally non-flammable at room temperature and 630 torr pressure. It is therefore unlikely to show flammability if released into room temperature air. If it is desired to provide an extra margin of safety against flammability, it would be possible to add a small amount (perhaps 5%) of a non-flammable component such as 1,1,3,3,3,-pentafluoropropene or $CF_3I$.

1,1,3,3,3,-Pentafluoropropene and Propyne
(Penta/Propyne)

This blend was tested at the following ratios by mole percent: 80/20 and 85/15. The 80/20 blend showed flammability over a substantial range in air at room temperature. The 85/15 blend showed no flammability in air at any concentration. Therefore, the borderline for flammability for this blend at room temperature lies between these concentrations, estimated at 83/17. Allowing for 5% changes in cryogenic composition due to fractionation, this gives an 88/12 blend as a possible cryogen. This corresponds to 96% by weight of 1,1,3,3,3-pentafluoropropene and 4% by weight of propyne. In one example, the ratio by weight for non-flammability is about 83% to about 96% 1,1,3,3,3-pentafluropropene to about 17% to about 4% propyne.

$CF_3I$ and 3,3,3,-Trifluoropropene ($CF_3I$/Tri)

This blend was tested at the following ratios by mole percent: 50/50; 40/60; 37.5/62.5; 35/65; and 30/70. The 35/65 and the 30/70 blends showed flammability at a range of concentrations in air at room temperature. The 50/50, 40/60 and 37.5/62.5 blends showed no flammability at any concentration in air at room temperature. Therefore, the borderline of flammability for this blend at room temperature is 37/63. Allowing for 5% changes in cryogenic composition due to fractionation, this gives a 42/58 blend as a possible cryogen. This corresponds to 50% by weight of $CF_3I$ and 50% by weight of 3,3,3-trifluoropropene. This blend has a lower percentage of $CF_3I$ than either Honeywell's H Fluid or Ikon A and is therefore likely to be less toxic. In one example, the ratio by weight for non-flammability is about 50% to about 60% $CF_3I$ to about 50% to about 40% 3,3,3,-trifluoropropene.

Another nonflammable blend we discovered, $CF_3I$/2-tetra, was found to require only 22% by weight of $CF_3I$ for non-flammability and therefore may be more attractive from the point of view of $CF_3I$ exposure.

$CF_3I$ and 2,3,3,3-Tetrafluoropropene

This blend was tested at the following ratios by mole percent: 0/100 (pure 2-tetra), 5/95, and 10/90. The reported LFL and UFL for pure 2-tetra in air at 100° C. are 5.0% and 14.5%, respectively (see B. Minor et al., "Compositions Comprising a Fluoroolefin," U.S. Patent Application Number 20060243945, Nov. 2, 2006, DuPont). At room temperature for pure 2-tetra, we found the LFL and UFL to be 7.0% and 13%. As expected, this range of flammable concentrations in air was narrower at room temperature than at 100° C. Somewhat surprising was the large difference we found in flammability at room temperature between 1-tetra and 2-tetra, given the fact that they have identical reported flammabilities at 100° C. (both have an identical reported LFL of 5.0% and UFL of 14.5%). While the 1-tetra lost its flammability as the temperature decreased from 100° C. to room temperature, we found that the 2-tetra retained much of its flammability, according to ASTM-681, as the temperature decreased. 1-tetra can be considered for use as a cryogen in pure form or with a slight addition of penta or $CF_3I$.

The pure 2-tetra showed flammability between 7% and 13% in air at room temperature according to ASTM E-681. The 5/95 and 7.5/92.5 blends of $CF_3I$ and 2-tetra showed flammability at narrow ranges of concentrations, while the 10/90 blend showed no flammability at any concentration in air at room temperature. The borderline of flammability for this blend was determined to be a ratio of about 9/9 1. Allowing for 5% changes in cryogenic composition due to fractionation, this gives a 14/86 blend as a possible cryogen. This corresponds to about 22% by weight of $CF_3I$ and about 78% by weight of 2,3,3,3-tetrafluoropropene. Of all the $CF_3I$ blends tested, this has the lowest weight percent of $CF_3I$ and therefore gives the lowest toxicity risk of exposure to $CF_3I$. It has less than half the weight percentage of $CF_3I$ compared to H-fluid or Ikon A. In one example, the ratio by weight for non-flammability is about 22% to about 99% $CF_3I$ to about 78% to about 1% 2,3,3,3-tetrafluoropropene. In another example, the ratio by weight for non-flammability is about 22% to about 50% $CF_3I$ to about 78% to about 50% 2,3,3,3-tetrafluoropropene. ASTM E-681 is known to be an extremely severe test of flammability. For example, perchloroethylene and trichloroethylene show some flammability over a certain range of concentrations in this test. However, these two chemicals exhibit no flammability by several other tests, are classified as nonflammable, and have been used for decades in million-pound quantities without flammability. Although 2,3,3,3-tetra shows flammability in the ASTM E-681 test at certain concentrations, the flammability risk in realistic scenarios has been shown to be minimal (Mark Spatz and Barbara Minor, "HFO-1234yf, A Low GWP Refrigeration for MAC," VDA Alternative Refrigeration Winter Meeting, Austria, 2008). In the absence of a very strong ignition source, the 2,3,3,3-tetrafluoropropene will not ignite, and the skin treatment system described herein does not contain any strong ignition sources. Therefore, pure 2,3,3,3-tetrafluoropropene could be used as a spray coolant.

$CF_3I$ and Propyne

This blend was tested at the following ratios by mole percent: 50/50, 60/40, 70/30, 80/20, and 90/10. All of the blends tested showed flammability at a range of concentrations in air at room temperature. In other words, there was no blend of these components tested that was nonflammable. Testing showed that less than 10% (estimated 8%) by moles propyne could be added to $CF_3I$. Allowing 5% for fractionation, this gives a 97/3 blend by moles corresponding to 99/1 by weight. In one example, the ratio by weight for non-flammability is about 97% to about 99% $CF_3I$ to about 3% to about 1% propyne.

Conclusions

There are quite a few attractive potential cryogens blends in addition to the pure cryogens to replace R-134a in a skin treatment apparatus. Table 4 below shows embodiments of pure chemicals and blend pairs that can be useful as cryogenic compositions in a skin treatment apparatus.

TABLE 4

Nonflammable low global warming cryogenic compositions

| | Blended with | | | | | | | |
|---|---|---|---|---|---|---|---|---|
| | By itself (pure) | 1,1-difluoro-ethane | 3,3,3-trifluoro-propene | 1,3,3,3-tetrafluoro-propene | 2,3,3,3-tetrafluoro-propene | 1,1,3,3,3-pentafluoro-propene | 1,2,3,3,3-pentafluoro-propene | trifluoro-methyl iodide |
| 1,1,3,3,3-pentafluoropropene | x | x | x | x | x | | | |
| 1,2,3,3,3-pentafluoropropene | x | x | x | x | x | | | |

TABLE 4-continued

Nonflammable low global warming cryogenic compositions

| | By itself (pure) | Blended with | | | | | | |
|---|---|---|---|---|---|---|---|---|
| | | 1,1-difluoro-ethane | 3,3,3-trifluoro-propene | 1,3,3,3-tetrafluoro-propene | 2,3,3,3-tetrafluoro-propene | 1,1,3,3,3-pentafluoro-propene | 1,2,3,3,3-pentafluoro-propene | trifluoro-methyl iodide |
| 1,3,3,3-tetrafluoropropene | x | | | | | x | x | x |
| 2,3,3,3-tetrafluoropropene | x | | | | | x | x | x |
| trifluoromethyl iodide | x | x | x | x | x | | | |

Pentafluoropropene (1,1,3,3,3- or 1,2,3,3,3-) may be an attractive cryogenic composition in pure form. 1,3,3,3-tetrafluoropropene may be blended with a small amount of a pentafluoropropene or $CF_3I$.

A pentafluoropropene could also be blended with 3,3,3-trifluoropropene.

Because there are two isomers of pentafluoropropene and two of tetrafluoropropene, there are four possible penta/tetra blends. It appears that all of them may be suitable. We tested two of these pairs (1,1,3,3,3-pentafluoropropene/1,3,3,3-tetrafluoropropene and 1,1,3,3,3-pentafluoropropene/2,3,3,3-tetrafluoropropene) and both appeared promising.

Of the two isomers of tetrafluoropropene, the 2,3,3,3 isomer has the advantage of lower boiling point and less potential for cryogen pooling during evaporation. However, it is flammable at room temperature and has a noticeable odor, while the 1,3,3,3 isomer is nonflammable at room temperature.

If a pentafluoropropene is otherwise attractive, but cost or cooling capacity is an issue, it could be blended with R-152a (about 82/18 by weight), which would both decrease the cost and increase the heat of vaporization.

Pure 2,3,3,3-tetrafluoropropene can be used as a cryogen in pure form and, the 1,1,3,3,3-pentafluoropropene/2-tetra (about 17/83 by weight) blend may also be considered.

Pure 3,3,3-trifluoropropene cannot be used as a cryogen in pure form because of its flammability at room temperature. However, a penta/tri blend may be considered.

The following blends may be considered: $CF_3I$/tri (about 50/50 by weight) and $CF_3I$/2-tetra (about 22/78 by weight).

Blends of $CF_3I$ with 3,3,3-trifluoropropene (50/50 by weight) or with 2,3,3,3-tetrafluoropropene (22/78 by weight) could be considered. The $CF_3I$/2-tetra blend has the lowest percentage of $CF_3I$ of any non-flammable blend studied so far and therefore, may be an attractive $CF_3I$-containing blend.

Penta/tetra blends appear very promising as replacement cryogens. Because there are two isomers each of penta and tetra, there are four possible penta/tetra combinations. Of the tetra isomers, 1-tetra has the advantage of very low flammability at room temperature, while 2-tetra has a more attractive boiling point.

It turns out that 1-tetra, even in pure form, has only the slightest flammability (being just at the verge of flammability) and addition of even 5% by moles (6% by weight) of 1,1,3,3,3-pentafluoropropene inerts it. This 95/5 blend may be attractive because pentafluoropropene is likely to be the more expensive component.

A penta/152a blend (about 82/18 by weight) may also be considered. This blend would have lower cost and improved cooling performance compared to pure penta. Either isomer of penta could be considered for blending with 152a.

In this effort, two isomers of tetrafluoropropene, one isomer of pentafluoropropene and one isomer of trifluoropropene were tested. Isomers were picked that appeared to have the most attractive physical properties as cryogens and to be the easiest to manufacture. However, there is another isomer of pentafluoropropene that was not tested in this effort. However, it may be desirable to conduct blend flammability tests on this isomer. This isomer may also be attractive for spray cooling.

Also, various mixtures of the non-flammable cryogens are contemplated for use as suitable cryogenic compositions for use in the skin treatment apparatus.

Although heat of vaporization data are not readily available for penta and tetra, refrigerants containing these components have about 20% lower cooling capacity than R134a (B. Minor et al., "Compositions Comprising a Fluoroolefin," U.S. Patent Application Number 20060243945, Nov. 2, 2006, DuPont). This makes it likely that they have lower heats of vaporization, and if so 20-25% greater quantities may be required for cryogen use. Preliminary performance tests of pure penta and a penta/2-tetra blend in a skin treatment apparatus have shown that larger quantities are required.

Accordingly, it would appear that several pure compounds and binary blends are potentially attractive as alternative cryogens. In addition, ternary blends that may be considered are listed in Table 5 below. The potential advantage of ternary blends is lower cost due to reduced use of more expensive nonflammable component.

TABLE 5

Ternary blends of the cryogenic compositions

| High-volatility flammable component | Nonflammable component | Low-volatility flammable component |
|---|---|---|
| 152a | 1,1,3,3,3-pentafluoropropene | 1,3,3,3-tetrafluoropropene |
| 152a | 1,1,3,3,3-pentafluoropropene | 3,3,3-trifluoropropene |
| 2,3,3,3-tetrafluoropropene | 1,1,3,3,3-pentafluoropropene | 1,3,3,3-tetrafluoropropene |
| 2,3,3,3-tetrafluoropropene | 1,1,3,3,3-pentafluoropropene | 3,3,3-trifluoropropene |

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative product and/or method and examples shown and described. Accordingly, departures may be made from such details without departing from the scope of the general inventive concept.

What is claimed is:

1. A method for cooling skin tissue comprising:
using a cryogenic composition in a skin treatment apparatus to cool heated skin during skin treatments, the cryogenic composition including
propyne in combination with one or more of the following: 1,1,3,3,3-pentafluoropropene, 1,2,3,3,3-pentafluoropropene, or trifluoroiodomethane.

2. The method of claim 1 wherein the cryogenic composition is a mixture of trifluoroiodomethane and propyne, with trifluoroiodomethane being present in an amount of about 97% to about 99% by weight of the composition.

3. The method of claim 1 wherein using a cryogenic composition in a skin treatment apparatus to cool heated skin during skin treatments comprises:
positioning an electrode of the skin treatment apparatus adjacent a skin surface, the skin treatment apparatus adapted to deliver energy via the electrode to tissue located beneath the skin surface;
applying energy to tissue located beneath the skin surface via the electrode; and
spraying the cryogenic composition against a non-patient side of the electrode to cool the tissue.

4. The method of claim 3 further including detecting a temperature of the electrode.

5. The method of claim 1 wherein the cryogenic composition is propyne in combination with 1,1,3,3,3-pentafluoropropene, 1,2,3,3,3-pentafluoropropene, or trifluoroiodomethane.

6. The method of claim 1 wherein the cryogenic composition is propyne in combination with 1,1,3,3,3-pentafluoropropene.

7. The method of claim 1 wherein the cryogenic composition is propyne in combination with 1,2,3,3,3-pentafluoropropene.

8. The method of claim 1 wherein the cryogenic composition is propyne in combination with trifluoroiodomethane.

* * * * *